United States Patent
Wegner et al.

(10) Patent No.: US 7,126,036 B2
(45) Date of Patent: Oct. 24, 2006

(54) THERMAL ISOMERIZATION OF LYCOPENE

(75) Inventors: Christoph Wegner, Kirchheim (DE); Michael John, Lambsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 477 days.

(21) Appl. No.: 10/466,477

(22) PCT Filed: Jan. 24, 2002

(86) PCT No.: PCT/EP02/00708

§ 371 (c)(1), (2), (4) Date: Jul. 16, 2003

(87) PCT Pub. No.: WO02/072509

PCT Pub. Date: Sep. 19, 2002

(65) Prior Publication Data

US 2004/0049082 A1    Mar. 11, 2004

(30) Foreign Application Priority Data

Jan. 26, 2001  (DE)  ................. 101 03 708

(51) Int. Cl.
*C07C 403/00* (2006.01)
(52) U.S. Cl. .................................... 585/351
(58) Field of Classification Search ................. 585/351
See application file for complete search history.

(56) References Cited

U.S. PATENT DOCUMENTS

| 2,849,507 A | * | 8/1958 | Otto et al. | ................. 585/351 |
| 5,166,445 A |  | 11/1992 | Meyer |  |
| 6,187,959 B1 |  | 2/2001 | Wegner et al. |  |

FOREIGN PATENT DOCUMENTS

| EP | 382 067 | 8/1990 |
| EP | 895 997 | 2/1999 |

OTHER PUBLICATIONS

Polgar, A. et al., "Isomerization of β-Carotene. Isolation of a Stereoisomer with Increased Adsorption Affinity", J. Am. Chem. Soc., 1942, vol. 64, 1856-1861.*

Doering et al., "Thermal Interconversions among 15-cis, 13-cis and all-trans-β-Carotene: Kinetics, Arrhenius Parameters, Thermochemistry, and Potential Relevance to Anticarcinogenicity of all-trans-β-Carotene", J. Am. Chem. Soc., 1995, vol. 117, 2747-2757.*

Muller et al., "(E/Z)-Isomeric carotenes", Pure & Appl. Chem., 1997, vol. 69, No. 10, 2039-2046.*

* cited by examiner

*Primary Examiner*—Thuan D Dang
(74) *Attorney, Agent, or Firm*—Novak Druce & Quigg, LLP

(57) ABSTRACT

The present invention relates to a process for the thermal isomerization of a mixture of all-E-lycopene and its Z isomers of any composition to increase the proportion of all-E, wherein the isomerization takes place in a polar solvent in which lycopene is only slightly soluble.

7 Claims, No Drawings

THERMAL ISOMERIZATION OF LYCOPENE

The present invention relates to a process for the thermal isomerization of a mixture of all-E-lycopene and its Z isomer of any composition lycopene is a carotenoid which occurs naturally inter alia in tomatoes.

It is an object of the present invention to develop an efficient method for isomerizing the Z form into the all-E form which does not have the described prior art disadvantages and makes it possible to use the more cost-effective E/Z synthons.

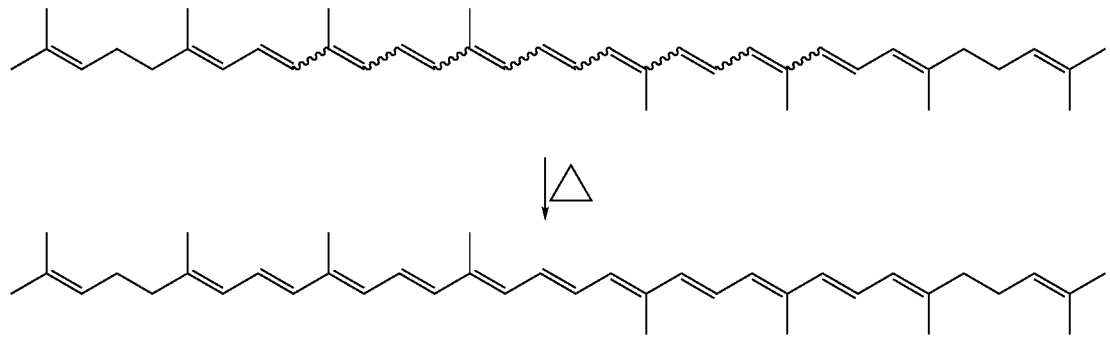

There is to date no method by which a mixture of Z isomers or else individual Z isomers of lycopene can be converted efficiently into the all-E form. Attempts to do this photochemically or thermally always lead to a mixture of various lycopene isomers.

The enhanced formation of Z isomers in the previous attempts to convert lycopene photochemically or thermally into the all-E form is attributable to the fact that the lycopene molecule is highly twisted in an S shape. Thus lycopene as all-E isomer achieves only a small thermodynamic energy advantage, which is significantly greater than for the corresponding Z isomers, in carotenoids having the planar conformation. These can then often be isomerized thermally into the all-E form (e.g. astaxanthin). lycopene, not having this energy advantage of the all-E form, therefore forms an isomer equilibrium in which all-E-lycopene is an isomeric form which is virtually equally energetically favored as are the many possible Z isomers, with the consequence that all-E levels fall greatly on attempts at isomerization (declining until the equilibrium is reached).

The synthesis of lycopene results in up to 50% of Z isomers, which is attributable to the fact that the $C_{15}$ phosphonium salt employed, which is attached twice to $C_{10}$ dialdehyde, has an E/Z ratio of 4:1 and the $C_{10}$ dialdehyde which is likewise employed has an E/Z ratio of from 96:4 to 97:3.

E/Z-Lycopene means hereinafter all-E-lycopene with any content of Z isomers.

For this reason, all described syntheses of all-E-lycopene (e.g. EP 895 997, EP 382 067) aim to prevent the formation of Z isomers even during the synthesis. This is possible only by elaborate syntheses, in some of which it is also necessary to introduce costly, pure E isomer building blocks.

EP 382 067 describes a process in which C15 phosphonium salts of lower alkanoic acids are prepared as intermediates, because the salts of strong acids generally afford poor E/Z selectivities and low yields of lycopene. The salts of the alkanoic acids must be converted back into the chlorides in an elaborate process using anion exchange before the final Wittig olefination. To achieve a high E/Z ratio in the lycopene it is additionally necessary to remove (Z) contents of the phosphonium salt by crystallization.

We have found that this object is achieved by a process for the thermal isomerization of a mixture of all-E-lycopene and its Z isomers of any composition to increase the proportion of all-E, wherein the isomerization takes place in a polar solvent in which lycopene is only slightly soluble.

The invention thus relates to a process for the thermal isomerization of all-E-lycopene and its Z isomers of any composition to increase the proportion of all-E, wherein the isomerization takes place in a polar solvent.

Previous attempts to isomerize lycopene have always been carried out in solutions. Since the thermodynamic stability of the all-E isomer of lycopene has, owing to a very twisted conformation, no, or only a vanishingly small, energetic advantage in this case however, a mixture of many Z isomers was always produced.

The process of the invention makes use of a suspension of lycopene in a polar solvent in which lycopene is only slightly soluble.

Polar solvents employed are alcohols such as $C_1$–$C_8$-alcohols, diols, polyols, amides, carbonates, sulfoxides or water.

$C_1$–$C_8$-Alcohols are, for example, methanol, ethanol, ethylene glycol, glycerol, propanol, isopropanol, butanol, tert-butanol, pentanol, hexanol, heptanol or octanol, and methanol, ethanol or butanol are preferably employed. An example of a diol which can be employed is ethylene glycol. Polyols mean, for example, polyethylene glycol. Examples of amides are formamide, acetamide, methylformamide, methylacetamide, dimethylformamide, dimethylacetamide or y-butyrolactone. Carbonates mean, for example, ethylene carbonate or propylene carbonate. An example of a sulfoxide which can be used is dimethyl sulfoxide.

The process of the invention exploits the effect that all-E-lycopene crystallizes very much better than the Z isomers in a solvent in which lycopene is virtually insoluble. For this purpose, the solvent must be so polar that the Z isomers are scarcely able to remain in solution but, owing to surface affinity, form an amorphous or oily layer around the all-E crystals. In this case it is possible, if the temperature is sufficiently high, for there to be selective isomerization of the Z isomers in this layer, because the all-E isomers bound in the crystal have a considerably higher isomerization activation energy. Owing to the local closeness to the all-E crystals, an all-E isomer which repeatedly arises by chance in the continuously dynamic isomerization process is immediately integrated into the crystal and thus escapes back-isomerization into a Z form. Overall, the isomerization equilibrium can thus be shifted toward the all-E isomer.

The solubility of lycopene should preferably be below 0.1% at room temperature. The isomerization temperature is between 40 and 180° C., preferably between 60 and 120° C. The isomerization can be carried out both under atmospheric pressure and under elevated pressure, preferably under pressures of from 1 to 6 bar.

A suspension of lycopene in a polar solvent in which lycopene is only slightly soluble is prepared immediately after a Wittig reaction by changing to this solvent by distillative solvent exchange, or by carrying out the Wittig reaction to give lycopene directly in this polar solvent.

It is then possible for lycopene, in various ratios of amounts in relation to the polar solvent, preferably as 5 to 20% strength suspension of lycopene in the polar solvent, to be isomerized by heating.

This can then be followed by three different variants: firstly, the suspension can be isomerized directly by heating. An alternative is to replace the volume of dichloromethane distilled out by adding alcohol, for example methanol, and subsequently to isomerize by heating. In the third variant, the solvent is changed to, for example, n-butanol, and then isomerization is carried out.

The experiments can be evaluated by filtering off the crystals after cooling the suspension, and washing, drying, weighing and determining the content by UV measurement.

If, for example, the solvent is changed from, for example, dichloromethane in which the lycopene is synthesized to methanol to generate a suspension which may contain any mixture of all-E-lycopene with Z isomers, and the latter is heated under reflux or else under superatmospheric pressure to elevated temperatures, then only the noncrystalline lycopene isomers are subject to permanent isomerization, whereas the lycopene incorporated in the crystal (all-E) is not. Whenever the free Z isomer is converted into an all-E isomer, it is incorporated into the crystal and is thus no longer available for back-isomerization.

It was possible to increase the all-E content in a mixture of 50% all-E-lycopene with 50% Z isomers to 75% in this way. Complete isomerization cannot be achieved because the 5Z isomer crystallizes about as well as all-E-lycopene, so that the ratio of all-E to 5Z cannot be influenced. All the other isomers are converted into these two. It was possible thus to increase the yield of lycopene crystals after filtration by 27 to 35%.

Since lycopene is only slightly soluble in most solvents, this process can in principle be carried out in almost any solvent. The only condition is that more than 70%, with more than 90% being better, of the all-E-lycopene must be in crystalline form at the chosen isomerization temperature.

The development of larger defined crystals during the isomerization leads to a considerable increase in the purity of the crystals. It was consequently possible to achieve phosphorus levels of <100 ppm even after the first crystallization. This is extremely surprising since crystallization took place from a solution containing two equivalents of triphenylphosphane. Normal lycopene types (without isomerization) have around 1000 ppm of phosphorus.

The advantages which can thus be achieved overall by the thermal lycopene isomerization method of the invention are as follows:
  distinctly higher yield of lycopene crystals
  it is possible to employ more cost-effective starting materials in the synthesis of lycopene because they no longer have to be pure E isomers
  increase in the proportion of all-E
  increase in the content The following examples are intended to explain the invention in detail but without restricting it thereto.

EXAMPLES

Example 1

Methanol (330 ml) was added to a solution of lycopene (44.0 g) with an all-E content of 53% in dichloromethane (317 g) at 40° C., and the dichloromethane was then distilled out (as azeotrope with MeOH, 0.94:6), continuously replacing the dichloromethane volume which was distilled out by methanol being fed into the reactor. The resulting suspension of lycopene in methanol was then heated under reflux for 40 h, carrying out an HPLC analysis after 16 h and after 40 h: the proportion of all-E was 67% after 16 h and 68% after 40 h. The proportion of 5Z was constant at 18% throughout. The suspension was then cooled to 0° C., filtered and washed with methanol (4×100 ml). After drying in a stream of nitrogen gas, it was possible to isolate 42.3 g of lycopene crystals with a content of 86% and a proportion of all-E of 76.3%. This corresponds to 36.4 g of lycopene.

Example 2

Methanol (330 ml) was added to a solution of lycopene (44.0 g) with an all-E content of 53% in dichloromethane (317 g) at 40° C., and the dichloromethane was then distilled out (as azeotrope with MeOH, 94:6). The resulting suspension of lycopene in methanol was then heated under reflux for 40 h, carrying out an HPLC analysis after 16, 23 and 40 h: the proportion of all-E was 64% after 16 h, 66% after 23 h and 71% after 40 h. The suspension was then cooled to 0° C., filtered and washed with methanol (4×100 ml).

After drying in a stream of nitrogen gas it was possible to isolate 42.3 g of lycopene crystals with a content of 92% and a proportion of all-E of 73.4%. This corresponds to 38.9 g of lycopene.

Example 3

Methanol (330 ml) was added to a solution of lycopene (44.0 g) with an all-E content of 53% in dichloromethane (317 g) at 40° C., and the dichloromethane was then distilled out (as azeotrope with MeOH, 94:6), continuously replacing the dichloromethane volume which was distilled out by methanol being fed into the reactor. The resulting suspension of lycopene in methanol was then heated at 95° C. under autogenous pressure (about 3 bar) for 12 h. The suspension was then cooled to 0° C., filtered and washed with methanol (4×100 ml). After drying in a stream of nitrogen gas it was possible to isolate 39.4 g of lycopene crystals with a content of 97% and a proportion of all-E of 81.2%. This corresponds to 38.2 g of lycopene.

Example 4

Methanol (330 ml) was added to a solution of lycopene (44.0 g) with an all-E content of 53% in dichloromethane (317 g) at 40° C., and the dichloromethane was then distilled out (as azeotrope with MeOH, 94:6). The resulting suspension of lycopene in methanol was then heated at 95° C. under autogenous pressure (about 3 bar) for 12 h. The suspension was then cooled to 0° C., filtered and washed with methanol (4×100 ml). After drying in a stream of nitrogen gas it was possible to isolate 44.0 g of lycopene crystals with a content of 99% and a proportion of all-E of 79.6%. This corresponds to 43.6 g of lycopene.

Example 5

Methanol (330 ml) was added to a solution of lycopene (44.0 g) with an all-E content of 53% in dichloromethane (317 g) at 40° C., and the dichloromethane was then distilled out (as azeotrope with MeOH, 94:6), continuously replacing the dichloromethane volume which was distilled out by methanol being fed into the reactor. The resulting suspension of lycopene in methanol was then heated at 120° C. under autogenous pressure (about 5 bar) for 6 h. The suspension was then cooled to 0° C., filtered and washed with methanol (4×100 ml). After drying in a stream of nitrogen gas it was possible to isolate 40.3 g of lycopene crystals with a content of 0.85% and a proportion of all-E of 87.5%. This corresponds to 35.3 g of lycopene.

Example 6

1-Butanol (330 ml) was added to a solution of lycopene (44.0 g) with an all-E content of 53% in dichloromethane (317 g) at 40° C., and the dichloromethane was then distilled out, continuously replacing the dichloromethane volume which was distilled out by 1-butanol being fed into the reactor. The resulting suspension of lycopene on 1-butanol was then heated at 95° C. for 15 h. The suspension was then cooled to 0° C., filtered and washed with methanol (4×100 ml). After drying in a stream of nitrogen gas, it was possible to isolate 32.9 g of lycopene crystals with a content of 100% and a proportion of all-E of 87.8%. This corresponds to 32.9 g of lycopene.

Example 7

Comparison: Without the isomerization step it was possible to obtain a weight of crystalline lycopene of only 30.0 g with a content of 95% and a proportion of all-E of 75.6%. This corresponds to 28.5 g of lycopene.

We claim:

1. A process for the thermal isomerization of a mixture of all-E-lycopene and its Z isomers of any composition to increase the proportion of all-E, wherein the isomerization takes place in a polar solvent.

2. A process as claimed in claim 1, wherein the isomerization takes place at between 60 and 180° C.

3. A process as claimed in claim 1, wherein the solubility of all-E-lycopene in the polar solvent at room temperature is less than 0.1%.

4. A process as claimed in any of claims 1, wherein $C_1$–$C_8$-alcohols, diols, polyols, amides, carbonates, sulfoxides or water are used as solvent.

5. A process as claimed in any of claim 1, wherein methanol, ethanol, isopropanol or butanol are used as solvent.

6. A process as claimed in any of claims 1, wherein more than 70% of the all-E-lycopene is in crystalline form at the chosen isomerization temperature.

7. A process as claimed in claim 1, wherein the lycopene mixture comprises 5Z-lycopene.

\* \* \* \* \*